(12) United States Patent
Farrell

(10) Patent No.: US 7,968,682 B2
(45) Date of Patent: Jun. 28, 2011

(54) DEGRADATION-RESISTANT FIBRINOGEN SEALANTS

(75) Inventor: David H. Farrell, Tualatin, OR (US)

(73) Assignee: Oregon Health & Science University, Portland, OR (US)

( * ) Notice: Subject to any disclaimer, the term of this patent is extended or adjusted under 35 U.S.C. 154(b) by 421 days.

(21) Appl. No.: 11/955,080

(22) Filed: Dec. 12, 2007

(65) Prior Publication Data

US 2008/0181878 A1  Jul. 31, 2008

Related U.S. Application Data

(60) Provisional application No. 60/874,310, filed on Dec. 12, 2006.

(51) Int. Cl.
*A61K 35/14* (2006.01)
*A61L 24/10* (2006.01)

(52) U.S. Cl. ... 530/382; 514/13.6; 514/14.7; 424/94.64; 435/214

(58) Field of Classification Search ............. 530/382; 514/13.6, 14.7; 424/94.64; 435/214
See application file for complete search history.

(56) References Cited

U.S. PATENT DOCUMENTS 5,739,288 A * 4/1998 Edwardson et al. .......... 530/382

OTHER PUBLICATIONS

Collet et al. 2004. Influence of gamma' Fibrinogen Splice Variant on Fibrin Physical Properties and Fibrinolysis Rate. Arterioscler. Thromb. Vasc. Biol. 24:382-386.*
Falls et al. 1997. Resistance of gammaA/gamma' Fibrin Clots to Fibrinolysis. J. Biol. Chem. vol. 272, No. 22, pp. 14251-14256.*
Buchta et al. 2005. Biochemical characterization of autologous fibrin sealants produced by CryoSeals and Vivostats in comparison to the homologous fibrin sealant product Tissucol/Tisseels. Biomaterials 26:6233-6241.*
Tisseel VH Fibrin Sealant Two-Component Fibrin Sealant, Vapor Heated, Kit. 2003. Baxter Healthcare Corp. p. 1-3.*
Moaddel, M., et al. "Interactions of human fibrinogens with factor XIII: roles of calcium and the gamma' peptide." Biochemistry. Jun. 6, 2000;39(22):6698-705.
Lovely, R.S., et al. "Association of gammaA/gamma' fibrinogen levels and coronary artery disease." Thromb Haemost. Jul. 2002;88(1):26-31.
Lovely, R.S., et al. "Fibrinogen gamma' chain binds thrombin exosite II." J Thromb Haemost. Jan. 2003;1(1):124-31.
Moaddel, M., et al. "The role of gamma A/gamma ' fibrinogen in plasma factor XIII activation." J Biol Chem. Oct. 13, 2000;275(41):32135-40.
Siebenlist, K.R., et al. "Studies on the basis for the properties of fibrin produced from fibrinogen-containing gamma' chains." Blood. Oct. 15, 2005;106(8):2730-6. Epub Jul. 7, 2005.
Podor, T.J., et al. "Incorporation of vitronectin into fibrin clots. Evidence for a binding interaction between vitronectin and gamma A/gamma' fibrinogen." J Biol Chem. Mar. 1, 2002;277(9):7520-8. Epub Dec. 14, 2001.
Siebenlist, K.R. "Response: Fibrinogen containing gamma' chains." Blood. Apr. 1, 2006;107(7):3011-2; author reply 3012.
Farrell, D.H. "Fibrinogen containing gamma' chains." Blood. Apr. 1, 2006;107(7):3011-2; author reply 3012.
Farrell, D.H. "Pathophysiologic roles of the fibrinogen gamma chain." Curr Opin Hematol. May 2004;11(3):151-5.

* cited by examiner

*Primary Examiner* — Taeyoon Kim
(74) *Attorney, Agent, or Firm* — Dann Dorfman Herrell & Skillman; Robert C. Netter, Jr.

(57) ABSTRACT

Provided are degradation-resistant fibrinogen sealants comprising a first composition comprising one or more of fibrinogen γA/γ' heterodimers and/or fibrinogen γ'/γ' homodimers and a second composition comprising thrombin and, optionally, degradation-resistant fibrinogen sealants disclosed herein may further comprise Factor XIII and calcium. Degradation-resistant fibrinogen sealants are suitable for the treatment of trauma, particularly vascular trauma.

28 Claims, 2 Drawing Sheets

DEGRADATION-RESISTANT FIBRINOGEN SEALANTS

This application claims priority under 35 U.S.C. §119(e) to U.S. Provisional Patent Application No. 60/874,310, filed on Dec. 12, 2006. The foregoing application is incorporated by reference herein.

This invention was made with United States Government support pursuant to Grant Number NIH/NHLBI 1 R29 HL053997 from the National Institutes of Health; the United States government has certain rights in the invention.

FIELD OF THE INVENTION

The present disclosure relates generally to the treatment of wounds, particularly vascular wounds. More specifically, the present disclosure provides degradation-resistant fibrinogen sealants having a first composition comprising fibrinogen γA/γ' heterodimers and/or fibrinogen γ'/γ' homodimers and a second composition comprising thrombin. Optionally, degradation-resistant fibrinogen sealants disclosed herein may further comprise Factor XIII and calcium.

BACKGROUND OF THE INVENTION

Several publications and patent documents are cited throughout the specification in order to describe the state of the art to which this invention pertains. Each of these citations is incorporated herein by reference as though set forth in full.

Blood clot formation occurs through the conversion of fibrinogen by thrombin and Factor XIIIa to form a cross-linked fibrin polymer. Fibrinogen is a 340,000-Da dimeric glycoprotein composed of six disulphide-linked polypeptide chains: two Aα($M_r$=65,000), two Bβ($M_r$=56,000), and two γ($M_r$=47,000). Fibrinogen is converted to fibrin through limited proteolysis by thrombin, which exposes polymerization sites in fibrinogen (Kudryk et al. (1974) *J. Biol. Chem.* 249: 3322-3325). The fibrin monomers spontaneously associate with each other to form the web-like fibrin clot (Blombäck (1996) *Thromb. Res.* 83:1-75).

Factor XIIIa is a plasma transglutaminase that strengthens the fibrin clot by forming covalent bonds between adjacent fibrin monomers (Lorand et al. (1993) *Methods Enzymol.* 222:22-35). Plasma Factor XIII is a 320,000-Da tetrameric protein composed of two polypeptide a chains ($M_r$=83,000) and two polypeptide b chains ($M_r$=80,000; Schwartz et al. (1973) *J. Biol. Chem.* 248:1395-1407). Factor XIII normally circulates as an inactive proenzyme until it is activated by thrombin cleavage of a 4000-Da activation peptide from each a subunit, which is followed by the dissociation of the b subunits. Activated factor XIII, or XIIIa, catalyzes the formation of γ-glutamyl-ε-lysine bonds between polypeptide chains in fibrin (Chen et al. (1969) *Proc. Natl. Acad. Sci. U.S.A.* 63:420-427). These cross-links strengthen the fibrin clot (Lorand (1972) *Ann. N. Y. Acad. Sci.* 202:6-30) and increase its resistance to lysis (Gaffney and Whitaker (1979) *Thromb. Res.* 14:85-94; Reed et al. (1992) *Thromb. Haemostasis* 68:315-320; Siebenlist and Mosesson (1994) *J. Biol. Chem.* 269:28414-28419).

Trauma is the leading cause of death for people between the ages of 1 and 44 in the United States (Bonne et al., eds. "Reducing the Burden of Injury: Advancing Prevention and Treatment." Committee on Injury Prevention and Control, Institute of Medicine (Washington, D.C., National Academy Press, 1999). The majority of deaths that occur during the first 48 hours following a traumatic event are the result of uncontrolled bleeding (Sauaia et al. (1995) "Epidemiology of Trauma Deaths: A Reassessment" *J. Trauma* 38:185-193). A common result of traumatic injury is disseminated intravascular coagulation (DIC), in which the activation of fibrinolytic enzymes causes the clot to dissolve. Massive hemorrhage can be resistant even to high doses of recombinant factor VIIa. The primary treatment of such injuries is therefore surgical repair, which is often aided by the use of fibrin sealants to stop hemorrhage. Fibrin sealants, such as BERIPLAST-P™ (Aventis-Behring), CROSSEAL™ (Johnson & Johnson), and TISSEEL™ (Baxter) may be applied during surgery from a two-syringe system. One syringe contains the fibrin precursor protein, fibrinogen, and the other syringe contains the clotting factor thrombin. These two components may be forced into a mixing chamber and act much like a two-part epoxy resin in which fibrinogen serves as the resin and thrombin serves as the catalyst. The mixture coagulates within minutes and stops bleeding from the wound site.

Fibrinolytic enzymes that are activated in DIC can, however, digest the applied fibrin sealant, resulting in re-bleeding of the wound even after initial control of hemorrhage. Furthermore, inhibitors of the fibrinolytic enzymes that are sometimes added to fibrin sealant, such as aprotinin, can be immunogenic and cause anaphylactic reactions. Therefore, there is still a need for degradation resistant fibrin sealants which avoid these drawbacks.

SUMMARY OF THE INVENTION

The present disclosure fulfills these and other related needs by providing degradation-resistant fibrinogen sealants that may be used in a wide variety of surgical applications including, for example, open surgery, trauma surgery, plastic surgery, general surgery, dental surgery, minimally invasive surgery, endoscopy, and microsurgery. Degradation-resistant fibrinogen sealants disclosed herein employ one or more fibrinogen dimers selected from a γA/γ' heterodimer and a γ'/γ' homodimer in combination with thrombin. Fibrinogen sealants may, optionally, also include one or more of Factor XIII and/or calcium.

Fibrinogen sealants are advantageously formulated as two separate compositions. A first composition contains one or more fibrinogen dimer (i.e. a fibrinogen γA/γ' heterodimer and/or fibrinogen γ'/γ' homodimer) and a second composition containing thrombin. The first composition may additionally contain Factor XIII. The second composition may additionally contain calcium (e.g., $CaCl_2$). When the two solutions are mixed, at the time of administration to a trauma patient in need thereof, the thrombin in the second composition converts the fibrinogen dimers to fibrin. In those embodiments further employing Factor XIII in the first composition, thrombin also converts the zymogen (inactive) form of Factor XIII to the active form that, in the presence of calcium, covalently cross-links the polymerized fibrinogen molecules.

In a particular embodiment of the instant invention, the compositions comprise at least one pharmaceutically acceptable carrier. Within certain aspects of these embodiments, the first composition may comprise one or more additional components selected from the group consisting of tranexamic acid, arginine hydrochloride, glycine, sodium chloride, sodium citrate, and calcium chloride.

The fibrinogen γA/γ' heterodimer and/or a γ'/γ' homodimer may be present in the first composition at a concentration of between about 5 mg/ml to about 200 mg/ml, between about 10 mg/ml to about 200 mg/ml, between about 25 mg/ml to about 150 mg/ml, or between about 40 mg/ml to about 130 mg/ml. In a particular embodiment, a fibrinogen γA/γ' heterodimer and/or a γ'/γ' homodimer is present in the first composition at a concentration of between about 65 mg/ml and about 115 mg/ml. In another embodiment, the fibrinogen γA/γ' heterodimer and/or a γ'/γ' homodimer is substantially pure. The fibrinogen γA/γ' heterodimer and/or a γ'/γ' homodimer may be the only fibrinogen present in the compositions of the instant degradation-resistant fibrinogen sealants.

In yet another embodiment, fibrinogen γ'/γ' may also be present in the first compositions as described above. Fibrinogen γ'/γ' may comprise between about 5% and about 90% of the total fibrinogen in a first composition. In a particular embodiment, γ'/γ' fibrinogen is present in the first composition at between about 10% and about 80% of the total fibrinogen, at between about 20% and about 70% of the total fibrinogen, or at about 30%, 40%, 50%, or 60% of the total fibrinogen.

Within those aspects wherein the first composition further comprises Factor XIII, it may be present at a concentration of from between about 10 U/ml and about 80 U/ml.

The pH of the first composition may be between about pH 5.0 and about pH 9.0, between about pH 5.5 and about pH 8.5, between about pH 6.0 and about pH 8.0, or between about pH 6.5 and about pH 7.5. In a particular embodiment, the pH of the first composition is between about pH 6.7 and about pH 7.2.

As indicated above, second compositions comprise thrombin. Thrombin is usually present in second compositions at a concentration of between about 4 IU/ml and about 1000 IU/ml, between about 10 IU/ml and about 150 IU/ml, or between about 15 IU/ml and about 120 IU/ml. Particularly, thrombin may be present in second compositions at a concentration of 25 IU/ml, 50 IU/ml, 75 IU/ml, or 100 IU/ml.

In those embodiments wherein calcium is present in the second composition, the concentration of calcium is typically between about 1 mM and about 70 mM, more typically between about 20 mM and about 60 mM, most typically between about 30 mM and about 50 mM. In some embodiments, a second solution may also contain human albumin, mannitol, and/or sodium acetate.

The pH of the second composition is usually between pH 5.0 to pH 9.0, between pH 5.5 to pH 8.5, between pH 6.0 to pH 8.0, between pH 6.5 to pH 7.5, or between pH 6.8 to pH 7.2.

Within certain aspects, degradation-resistant fibrinogen sealants disclosed herein may further employ one or more fibrin I and/or fibrin II monomer(s). Thus, for example, fibrin I monomers and/or fibrin II monomers may be prepared in advance of sealant application from fibrinogen using, for example, a proteolytic enzyme such as thrombin.

DETAILED DESCRIPTION OF THE INVENTION

Figure 1:
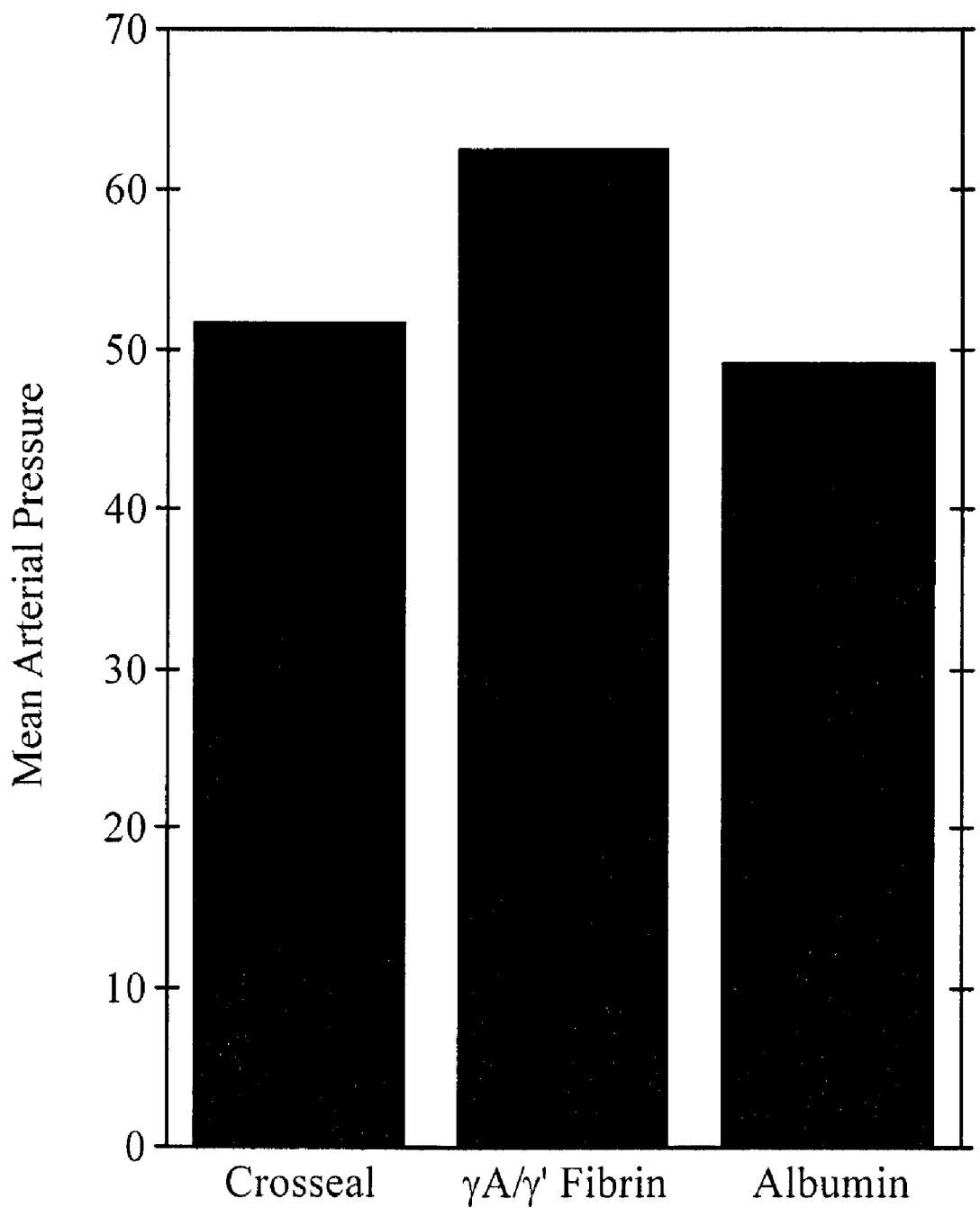
FIG. 1 is a graph representing the mean arterial pressure in pigs following aortic injury and treatment with CROSSEAL™ fibrinogen sealant, a degradation-resistant γA/γ' fibrin sealant of the present invention, or albumin.

The present disclosure is predicated on the observation that degradation-resistant fibrinogen sealants may be prepared from a combination of one or more γA/γ' fibrinogen heterodimers and/or γ'/γ' fibrinogen homodimers. Thus, the present disclosure provides degradation-resistant fibrinogen sealants employing a first composition comprising one or more γA/γ' fibrinogen heterodimer and/or γ'/γ' fibrinogen homodimer and optionally further comprising, without limitation, at least one pharmaceutically acceptable carrier, antibiotic, stabilizer, Factor XIII, tranexamic acid, arginine hydrochloride, glycine, sodium chloride, sodium citrate, and/or calcium chloride and a second composition comprising thrombin and optionally further comprising, without limitation, at least one pharmaceutically acceptable carrier, antibiotic, stabilizer, and/or calcium.

Fibrinogen is a 340,000-Da dimeric glycoprotein composed of six disulphide-linked polypeptide chains: two Aα($M_r$=65,000), two Bβ($M_r$=56,000), and two γ($M_r$=47,000). "A" and "B" represent two small amino terminal peptides, known as fibrinopeptide A and fibrinopeptide B, respectively. The formation of insoluble fibrin clots (e.g., crosslinked fibrin II polymer) is believed to begin with fibrinogen being converted by thrombin to fibrin I monomer. This conversion involves thrombin-mediated cleavage of the 16 amino acid fibrinopeptide A from each of the two Aα chains of fibrinogen, producing two α-chains each with a new N-terminus. It is believed that the fibrin I monomer can spontaneously polymerize with other fibrin I or fibrin II monomers.

The next step in the formation of fibrin clots is believed to involve the conversion of fibrin I monomer to fibrin II monomer. This step involves the thrombin-mediated cleavage of the fibrinopeptide B from each of the two Bβ chains of fibrin I. Fibrin II monomers, like fibrin I monomers, can spontaneously polymerize with other fibrin II or fibrin I monomers. Activated Factor XIIIa covalently crosslinks adjacent fibrin II monomers in the fibrin II polymer. Factor XIIIa is also capable of crosslinking fibrin I monomers in a fibrin polymer.

In plasma-derived fibrinogen, there are two alternatively spliced gamma chains, γA and γ'. The γ' chain arises from alternative processing of the γ chain mRNA that leads to the translation of a polypeptide with a 20-amino acid sequence substituted for the carboxyl-terminal four amino acids of the γA chain (Chung and Davie (1984) *Biochemistry* 23:4232-4236; Fornace et al. (1984) *J. Biol. Chem.* 259:12826-12830). In human plasma, about 90% of the fibrinogen present is γA/γA -fibrinogen, and the remaining 10% is γA/γ'-fibrinogen. The γ' chain binds to Factor XIII (Siebenlist et al. (1996) *Biochemistry* 35:10448-10453).

Both the rate of clotting and the rate of lysis are significantly decreased in γA/γ' fibrin clots as compared to γA/γA fibrin clots (Falls and Farrell (1997) *J. Biol. Chem.* 272:14251-14256). Clots made from γA/γ' fibrinogen in the presence of Factor XIII clot more slowly and subsequently lyse more slowly. Clot stability is enhanced further in the presence of supraphysiological concentrations of Factor XIII. Fibrinogen can polymerize into a clot or gel, which is able to act as a sealant, glue, hemostat, or wound healing matrix in vitro and in vivo.

Definitions

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "substantially pure" refers to a preparation comprising at least 50-60% by weight of a given material (e.g., nucleic acid, oligonucleotide, protein, etc.). More preferably, the preparation comprises at least 75% by weight, more preferably about 90-95% by weight, and more preferably about 99% by weight of the given compound. Purity is measured by methods appropriate for the given compound (e.g., chromatographic methods, agarose or polyacrylamide gel electrophoresis, HPLC analysis, and the like).

The term "isolated protein" or "isolated and purified protein" refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

The term "gene" refers to a nucleic acid comprising an open reading frame encoding a polypeptide, including both exon and (optionally) intron sequences. The nucleic acid may also optionally include non coding sequences such as promoter or enhancer sequences. The term "intron" refers to a DNA sequence present in a given gene that is not translated into protein and is generally found between exons.

As used herein, an "instructional material" includes a publication, a recording, a diagram, or any other medium of expression which can be used to communicate the usefulness of the composition of the invention for performing a method of the invention.

The term "antibiotics" refers to, without limitation, β-lactams (penicillins and cephalosporins), vancomycins, bacitracins, macrolides (erythromycins), lincosamides (clindomycin), chloramphenicols, tetracyclines (e.g., immunocycline, chlortetracycline, oxytetracycline, demeclocycline, methacycline, doxycycline and minocycline), aminoglycosides (e.g., gentamicins, amikacins, and neomycins), amphotericins, cefazolins, clindamycins, mupirocins, sulfonamides and trimethoprim, rifampicins, metronidazoles, quinolones, novobiocins, polymixins and gramicidins and the like and any salts or variants thereof.

The term "stabilizer" refers to a chemical agent (e.g., protein or polysaccharide) that assists to preserve or maintain the biological structure and/or biological activity of a protein. Examples of stabilizers include, without limitation, hydroxyethyl starch (hetastarch), serum albumin, gelatin, collagen, recombinant albumin, recombinant gelatin, recombinant collagen, non-oxidizing amino acid derivatives (e.g., tryptophan derivatives, such as N-acetyl-tryptophan), caprylates, polysorbates, amino acids, and divalent metal cations (e.g., $Zn^{2+}$), and cresols.

The term "pharmaceutically acceptable carrier" includes any and all solvents, dispersion media and the like which may be appropriate for the desired route of administration of the pharmaceutical composition. The use of such media for pharmaceutically active substances is known in the art. Except insofar as any conventional media or agent is incompatible with the compounds to be administered, its use in the pharmaceutical preparation is contemplated. A "carrier" refers to, for example, a diluent, adjuvant, excipient, auxiliary agent or vehicle with which an active agent of the present invention is administered. Examples of pharmaceutically acceptable carriers include, without limitation, water, buffered saline, ethanol, polyol (for example, glycerol, propylene glycol, liquid polyethylene glycol and the like), dimethyl sulfoxide (DMSO), oils, detergents, suspending agents or suitable mixtures thereof. Suitable pharmaceutically acceptable carriers and formulations are described in Remington's Pharmaceutical Sciences, 19th Ed. (Mack Publishing Co., Easton, 1995) and "Remington: The Science And Practice Of Pharmacy" by Alfonso R. Gennaro (Lippincott Williams & Wilkins, 2005).

Preparation of Degradation-Resistant Fibrinogen Sealants

Degradation-resistant fibrinogen sealants disclosed herein include a first composition comprising one or more of fibrinogen γA/γ' heterodimers and/or fibrinogen γ'/γ' homodimers and a second composition comprising thrombin. As indicated above, degradation-resistant fibrinogen sealants may additionally include, in a first composition, Factor XIII and, in a second composition, calcium (e.g., $CaCl_2$). Degradation-resistant fibrinogen sealants may be used in many applications including, for example, open surgery, trauma surgery, plastic surgery, general surgery, dental surgery, minimally invasive surgery, endoscopy, and microsurgery.

When the first composition and the second composition are mixed, the thrombin converts fibrinogen to fibrin. In some embodiments, thrombin also converts the zymogen (inactive) form of Factor XIII to the active form that, in the presence of calcium, covalently cross-links the polymerized fibrinogen molecules.

A fibrinogen γA/γ' heterodimer and/or a fibrinogen γ'/γ' homodimer may be present in the first composition at a concentration of between about 5 mg/ml to about 200 mg/ml, between about 10 mg/ml to about 200 mg/ml, between about 25 mg/ml to about 150 mg/ml, or between about 40 mg/ml to about 130 mg/ml. Particularly, a fibrinogen γA/γ' heterodimer and/or a γ'/γ' homodimer is present in the first composition at a concentration of between about 65 mg/ml and about 115 mg/ml. Suitable concentrations of fibrinogen γA/γ' heterodimers and/or a fibrinogen γ'/γ' homodimers may be achieved by precipitation using ethanol (EtOH) and low temperature (Dahlstrom et al. (1992) *Plast. Reconstr. Surg.* 89:968-972). Other precipitation methods may also be suitably employed for concentrating solutions comprising fibrinogen γA/γ' heterodimers and/or a fibrinogen γ'/γ' homodimers (such as, e.g., glycine or ammonium sulphate precipitation).

Fibrinogen γ'/γ' may comprise between about 0% and about 100% of the total fibrinogen in a first composition, between about 5% and about 90%, between about 10% and about 80% of the total fibrinogen, or between about 20% and about 70% of the total fibrinogen. In a particular embodiment, fibrinogen γ'/γ' may be present in the first composition at about 30%, 40%, 50%, or 60% of the total fibrinogen. If the fibrinogen is isolated from plasma, fibrinogen γ'/γ' may be present in trace amounts.

Fibrinogen γA/γA may also be present in the first composition. Fibrinogen γA/γA possesses degradation resistance properties similar to unfractionated fibrinogen. Accordingly, the addition of fibrinogen γA/γA to the first composition at different ratios to fibrinogen γA/γ' and γ'/γ' modulates the degradation resistance (e.g., an increase in the ratio of fibrinogen γA/γA would decrease the resistance to degradation). Fibrinogen γA/γA may comprise between about 5% and about 90% of the total fibrinogen is a first composition, between about 10% and about 80% of the total fibrinogen, or between about 20% and about 70% of the total fibrinogen. In a particular embodiment, fibrinogen γA/γA may be present in the first composition at about 30%, 40%, 50%, or 60% of the total fibrinogen.

Fibrinogen may be derived from pooled plasma, such as pooled human plasma. Fibrinogen may also be obtained from single-donor and autologous sources (e.g., from blood banks). The fibrinogen can be concentrated from the plasma by cryoprecipitation and precipitation using various reagents including, for example, poly(ethylene glycol), diethyl ether, ethanol, ammonium sulfate, and glycine. In a particular embodiment, the γA/γ' and γ'/γ' fibrinogen are separated from γA/γA fibrinogen. The γA/γ' and γ'/γ' fibrinogen may be separated, for example, by ion-exchange (Mosesson et al. (1972) J. Biol. Chem., 247:5223-5227) or affinity chromatography using an anti-γ' antibody such as 2.G2.H9 (Lovely et al. (2002) Thromb. Haemost., 88:26-31).

Fibrinogen may also be produced by chemical synthesis (see, e.g., Merrifield, (1963) J. Chem. Soc. 85:2149-2154; Hunkapillar et al., (1984) Nature 310:105-111) or by a recombinant process. For example, recombinant fibrinogen may be produced in the body fluids of transgenic animals as taught by WO 95/23868, which is herein incorporated by reference in its entirety. For example, fibrinogen may be recombinantly produced in the milk of placental mammals such as sheep, pigs, cattle goats, rabbits, and camels.

Genetic engineering may be used to produce fibrinogen and fibrin monomers in comparatively high yields. Heterologous expression of fibrinogen and fibrin chains also allows the construction of mutations that can mimic, for example, naturally occurring fibrin variants.

Each of the three polypeptide chains of fibrinogen (Aα, Bβ, and γ) is coded by a separate gene. Nucleotide sequences encoding fibrinogen, thrombin, Factor XIII, or other genes can be constructed using any known method. For example, nucleotide sequences can be chemically synthesized or synthesized using polymerase chain reaction (PCR) amplification (see, e.g., Gelfind, "PCR Technology: Principles and Applications for DNA Amplification" (Ed., H. A. Erlich, Stockton Press, N.Y.,1989); "Current Protocols in Molecular Biology" Vol. 2, Ch. 15 (Eds. Ausubel et al., John Wiley & Sons (1988); Horton et al. (1989) Gene 77:61-68).

Nucleotide sequences can also be constructed using recombinant DNA techniques (see, e.g., Sambrook et al., "Molecular Cloning: A Laboratory Manual" $2^{nd}$ ed., Cold Spring Harbor Laboratory, Cold Spring Harbor, N.Y., 1989). Vectors containing one or more nucleotide sequence may also be constructed. Possible vectors include, but are not limited to, plasmids, cosmids, or modified viruses or bacteriophages. These vectors may be used to transfect a procaryotic or eucaryotic host cell.

The cDNAs for each of the fibrinogen chains may be prepared and expressed in procaryotic organisms (Chung et al. (1983) Ann. N.Y. Acad. Sci. 408:449-456; Rixen et al., (1983) Biochemistry 22:3227-3244; Chung et al. (1983) Biochemistry 22:3244-3250; and Chung et al. (1983) Biochemistry 22:3250-3256). Each human fibrinogen chain is typically introduced separately (Huang et al. (1983) J. Biol. Chem. 268:8919-8926; Roy et al. (1992) J. Biol. Chem. 267:23151-23158; Roy et al. (1991) J. Biol. Chem., 266:4758-4763). Alternatively, human fibrinogen chains may be introduced in combination into expression plasmids and transfected into eukaryotic cells (Farrell et al. (1991) Biochemistry 30:9414-9420; Hartwig and Danishefsky (1991) J. Biol. Chem. 266: 6578-6585; Huang et al. (1983) J. Biol. Chem. 268:8919-8926; Roy et al. (1991) J. Biol. Chem. 266:4758-4763).

Suitable plasmids for use in expressing recombinant human fibrinogen have been described (see, e.g., Rixen et al. (1983) Biochemistry 22:3237-3244; Chung et al. (1983) Biochemistry 22:3244-3250; Chung et al. (1983) Biochemistry 22:3250-3256). Recombinant fibrinogen chains may be expressed in E. coli. (see, e.g., Bolyard and Lord (1988) Gene 66:183; Bolyard and Lord (1989) Blood 73:1202-1206; Lord and Fowlkes (1989) Blood 73:166-171).

Eukaryotic cells carrying expression plasmids encoding individual fibrinogen chains have been shown to synthesize the encoded fibrinogen chains and to result in the intracellular formation of dimeric chain molecules, e.g., Aα, Bβ, or γ dimers (Roy et al. (1990) J. Biol. Chem. 265:6389-6393; Zhang and Redman (1992) J. Biol. Chem. 267:21727-21732). When appropriate plasmids containing genes encoding all three human fibrinogen chains are transferred into the same cell, then not only are all three chains expressed but the polypeptide chains associate in pairs and intact fibrinogen is secreted into the surrounding medium (Farrell et al. (1991) Biochemistry 30:9414-9420; Roy et al. (1991) J. Biol. Chem. 266:4758-4763; Hartwig and Danishefsky (1991) J. Biol. Chem. 266:6578-6585). The secreted recombinant fibrinogen is functional in forming fibrin polymers.

Fibrinogen is naturally synthesized by, for example, liver and megakaryocyte cells. Transformed liver cells maintained in culture are able to continue fibrinogen synthesis and secretion (Otto et al. (1987) J. Cell Biol. 105:1067-1072; Yu et al. (1987) Thromb. Res. 46:281-293; Alving et al. (1982) Arch. Biochem. Biophys. 217:19). Hep G2 cells synthesize an excess of Aα and γ chains over Bβ chains, but the introduction of an additional expression vector encoding β chains resulted in the formation of trimeric complexes (AαBβγ) that adopt the correct folding and intrachain disulfide bonding patterns (Roy et al. (1990) J. Biol. Chem. 265:6389-6393). The AαBβγ trimeric complexes from the Hep G2 cells associate in pairs to form intact fibrinogen molecules that become glycosylated and are secreted from the cell (Huang et al. (1993) J. Biol. Chem. 268:8919-8926).

Fibrinogen may also be produced in eukaryotic cells that do not normally synthesize fibrinogen in significant quantities. For example, eukaryotic cells known to be capable of assembling and secreting recombinant fibrinogen include baby hamster kidney cells (BHK), COS cells and Chinese hamster ovary cells (CHO; Roy et al., (1991) J. Biol. Chem. 266:4758-4763; Hartwig and Danishefsky (1991) J. Biol. Chem. 266:6578-6585; Farrell et al. (1991) Biochemistry 30:9414-9420). Methods known to those of skill in the art may be used to increase the output of recombinant proteins from transfected cells.

Within those aspects wherein the first composition further comprises Factor XIII, it is typically present at a concentration of from between about 10 U/ml and about 80 U/ml. Factor XIII may be purified from pooled plasma. Factor XIII may also be produced by a recombinant process. For example, recombinant Factor XIII may be produced by host cells such as microbial cells (e.g., yeast cells) or mammalian cells. Methods for producing recombinant Factor XIII are disclosed in EP-A-0268772, which is herein incorporated by reference in its entirety.

Factor XIII is often co-purified with fibrinogen. For example, fibrinogen may be purified by chromatography using DEAE-cellulose and may be further purified by GPRPC-agarose chromatography (Falls and Farrell (1997) *J. Biol. Chem.* 272:14251-14256). Factor XIII co-purifies with γA/γ' fibrinogen on DEAE-cellulose (Siebenlist et al. (1996) *Biochemistry* 35:10448-10453), presumably by binding directly to the γ' chain in γA/γ' fibrinogen. Factor XIII is depleted from γA/γ' fibrinogen purified further on GPRPC-agarose (Falls and Farrell (1997) *J. Biol. Chem.* 272:14251-14256).

The pH of the first composition is usually between about pH 5.0 and about pH 9.0, between about pH 5.5 and about pH 8.5, between about pH 6.0 and about pH 8.0, between about pH 6.5 and about pH 7.5, or between about pH 6.7 and about pH 7.2.

As indicated above, degradation-resistant fibrinogen sealants employ a second composition comprising thrombin. Thrombin is usually present in second compositions at a concentration of between about 4 IU/ml and about 1000 IU/ml, between about 10 IU/ml and about 150 IU/ml, or between about 15 IU/ml and about 120 IU/ml. In a particular embodiment, thrombin is present in second compositions at a concentration of 25 IU/ml, 50 IU/ml, 75 IU/ml, or 100 IU/ml. Thrombin may be purified from, for example, bovine or human sources. Thrombin may also be produced by a recombinant process. For example, recombinant thrombin may be produced in mammalian cells, such as CHO cells. Processes for the production of thrombin are disclosed in U.S. Pat. Nos. 5,476,777; 5,502,034 and 5,572,692 which are herein incorporated by reference in their entirety.

In those embodiments wherein calcium is present in the second composition, the concentration of calcium may be between about 1 mM and about 70 mM, between about 20 mM and about 60 mM, or between about 30 mM and about 50 mM.

In some embodiments, a second composition of a degradation-resistant fibrinogen sealant may also contain human albumin, mannitol, and/or sodium acetate. The pH of the second composition is usually between pH 5.0 to pH 9.0, between pH 5.5 to pH 8.5, between pH 6.0 to pH 8.0, between pH 6.5 to pH 7.5, or between pH 6.8 to pH 7.2.

Within certain aspects, degradation-resistant fibrinogen sealants disclosed herein may further employ one or more fibrin I and/or fibrin II monomer(s). Thus, for example, fibrin I monomers and/or fibrin II monomers may be prepared in advance of sealant application from fibrinogen using, for example a proteolytic enzyme such as thrombin.

Fibrin I and fibrin II monomers can be prepared from fibrin polymer. For example, fibrin polymer can be dissolved using a weak acid solution and the resulting fibrin monomer can be lyophilized to a fine powder. The powder can be redissolved in a weak acid and induced to repolymerize by the addition of an alkali buffer. Alternatively or additionally, the powdered fibrin monomers can be dissolved in a chaotropic solution, e.g., urea, to a very high concentration (e.g., in excess of 150 mg/ml) and induced to repolymerize by the addition of water.

As will be recognized, fibrin gel structure can be modified by many different formulation variables including fibrinogen concentration, Factor XIII concentration, thrombin concentration, pH, ionic strength, and additives. For example, a fibrin sealant may additionally contain, for example, coagulation factors, amino acids, fibronectin, plasminogen, aprotinin, albumin, heparin, creatine, sodium citrate, anti-fibrinolytic agents, stabilizers, antibiotics, antibodies, anti-inflammatory compounds, cytokines, hormones, interferon, protease inhibitors, steroids, anesthetic, vitamins, chemotherapeutics, and fibroblastic growth factors, NaCl, arginine, tranexamic acid, and glycine.

Administration of Degradation-Resistant Fibrinogen Sealants

The degradation-resistant fibrinogen sealants disclosed herein may be administered in any manner including, for example, topically, parenterally, or intravenously. For example, for topical administration, a solution containing fibrinogen, thrombin or both may be applied to the tissue. The solution may be applied topically in any manner including, spraying or dripping the solution onto the tissue. Typically, the solution is applied in short bursts (0.1-0.2 ml) to produce a thin, even layer. If the hemostatic effect is not complete, a second layer may be applied. The amount of sealant required depends upon the area of tissue to be treated and the method of application.

Degradation-resistant fibrinogen sealants are applied as two or more compositions, typically the compositions are applied simultaneously in approximately equal volumes. Typically, the compositions are admixed upon application.

In some embodiments, the solutions may be applied, for example, using a multi-barreled syringe, (e.g., a double-barreled syringe), a spray tip (PANTAJECT® with a spray tip), a spray catheter (e.g., an ENDOFLEX® spray catheter with an ENDOFLEX® spray tip), a catheter (e.g., a CATHEJECT™ dual lumen endoscopic catheter, a flexible PvB catheter), a cannula (a CATHEJECT™ dual lumen cannula), or a probe (e.g., an ENDOFLEX® double-lumen probe).

Standard surgical techniques for hemorrhagic control, including suture, ligature, and cautery, may be used prior to the application of the sealant. Excess blood may be removed from the site of application, if possible, before applying the fibrin sealant.

Fibrinogen may also be administered intravenously. For example, fibrinogen may be injected intravenously to control hemorrhage. When a subject is bleeding excessively, for example due to trauma, it is often necessary to replace their fibrinogen by injection of cryoprecipitate. Fibrinogen injected intravenously could be used, for example, as a replacement or adjunct therapy to cryoprecipitate injection in transfusion medicine.

The fibrinogen to be administered intravenously may be administered as a composition. For example, fibrinogen may be formulated in a saline buffer. The concentration of fibrinogen in the composition may be 1-100 mg/ml. The concentration of fibrinogen in the composition may be about 5 mg/ml, 10 mg/ml, 15 mg/ml, or 20 mg/ml.

Fibrinogen γA/γ' may comprise between about 0% and about 100% of the total fibrinogen in a first composition. γA/γ' fibrinogen may be present in the first composition at between about 5% and 90% of the total fibrinogen, between about 10% and about 80% of the total fibrinogen, between about 20% and about 70% of the total fibrinogen, or at about 30%, 40%, 50%, or 60% of the total fibrinogen.

The indications for intravenous administration of fibrinogen are the same or similar to the indications for injection of cryoprecipitate. For example, fibrinogen may be administered intravenously when fibrinogen concentration in the blood plasma reaches below a certain critical cutoff.

Degradation-resistant γA/γ' and/or γ'/γ' fibrinogen sealants will result in decreased pathophysiologic sequelae of uncontrolled hemorrhage. A significantly more stable blood pressure will be maintained, as well as heart rate. Decreased blood loss will result in decreased loss of blood cells, resulting in a higher hematocrit. In addition, improved maintenance of clotting parameters measured in the activated partial thromboplastin time, prothrombin time, and thromboelastogram due to decreased loss of clotting factors from dilution and consumption are expected. Blood chemistries will also be maintained closer to normal ranges, and resuscitation fluid (lactated Ringer's solution) use should decrease.

Kit

The present invention also includes kits for the practice of the methods of the invention. The kits of the instant invention include the degradation-resistant fibrinogen sealants and a device for administering the compositions of the sealant. The first and second compositions may be provided in separate containers or may be provided "pre-loaded" in the device for administration. For example, the first and second compositions may be contained in a double-barreled syringe within the kit, ready for administration. Exemplary devices for the administration of the degradation-resistant fibrinogen sealants of the instant invention are described hereinabove.

In a particular embodiment, the kits further comprise at least one component selected from the group consisting of instruction material, wound dressing (e.g., without limitation, a bandages, gauzes, and sponges), sutures, other blood clotting compounds, wound cleaning agents (e.g. alcohol, saline, and means of irrigation (e.g., squirt bottle)), tourniquets, pain killers (e.g., analgesics such as narcotic analgesics (e.g., morphine), non-narcotic analgesics (e.g., aspirin and acetaminophen), and narcotic antagonistic analgesics), and antibiotics.

The following Examples are provided to illustrate the present invention, but are not meant to limit the invention in any way.

Example 1

Purification of γA/γ' and γA/γA Fibrinogen

Plasminogen-free human plasma fibrinogen (Calbiochem) was dissolved in 39 mM Tris-$PO_4$, pH 8.6, containing 5 mM ε-aminocaproic acid (EACA) and 0.2 mM phenylmethylsulfonyl fluoride (PMSF) and dialyzed into the same buffer at 4° C. Insoluble residue was removed by centrifugation at 10,000×g for 30 min at 4° C. The γA/γ' and γA/γA forms of fibrinogen were separated using DEAE-cellulose (Finlayson et al., (1960) *J. Clin. Invest.* 39:1837-1840). Briefly, the fibrinogen solution was adsorbed to a column of DEAE-cellulose (6×20 cm) and eluted with a 1200-ml exponential gradient generated in a 600-ml constant volume mixing chamber from the starting buffer (39 mM Tris-$PO_4$, pH 8.6; 5 mM EACA; and 0.2 mM PMSF) to the final buffer (193 mM Tris-$PO_4$, pH 4.6; 5 mM EACA; and 0.2 mM PMSF). The absorbance was monitored at 280 nm, and 11-ml fractions were collected. The elution profile showed two peaks; γA/γA fibrinogen composed the first peak and γA/γ' fibrinogen composed the second smaller peak.

γA/γ' and γA/γA may be further purified using a glycine-L-proline-L-arginine-L-proline-L-cysteine (GPRPC)-agarose affinity resin (Farrell and Thiagarajan (1994) *J. Biol. Chem.* 269:226-231). Briefly, the resin may be prepared by reacting 10 mg of glycine-L-proline-L-arginine-L-proline-L-cysteine peptide (Howard Hughes Medical Institute Biopolymer Laboratory, Seattle, Wash.) with 10 ml of 5-thio-2-nitrobenzoate-agarose (Pierce) according to the manufacturer's protocol. The dialyzed γA/γ' or γA/γA fibrinogen pool from DEAE-cellulose is adsorbed to a column (3 ml) of GPRPC-agarose, washed with 100 mM NaCl, 50 mM Tris-$PO_4$, pH 7.8, 5 mM EACA, 0.2 mM PMSF, and then washed with 2 M NaBr, 50 mM Tris-$PO_4$, pH 7.8, 5 mM EACA, 0.2 mM PMSF. The fibrinogen is eluted in 1-ml fractions with 2 M NaBr, 20 mM citrate, pH 5.3, 5 mM EACA, 0.2 mM PMSF and immediately neutralized with 0.02 volume of 2M Tris-HCl, pH 8.0. The fibrinogen fractions are dialyzed into 137 mM NaCl, 2.7 mM KCl, 10 mM HEPES, pH 7.4, 1 mM $CaCl_2$ and stored at −70° C.

Example 2

Preparation of a γA/γ° Fibrin Sealant

A first solution containing γA/γ' fibrinogen may be prepared from γA/γ' fibrinogen purified as described in Example 1. The γA/γ' fibrinogen may be treated with aluminum hydroxide gel to adsorb the Vitamin K dependent clotting factors. The γA/γ' fibrinogen may additionally or alternatively be incubated with a solvent detergent (SD) mixture consisting of 1% tri-n-butyl phosphate and 1% Triton X-100 for inactivation of enveloped viruses. The solvent detergent reagents may then be removed by castor oil extraction and reverse phase chromatography, for example a C-18 column, and the preparation may be treated by pasteurization.

Prior to pasteurization, sucrose (1.8 g/g column filtrate) and glycine (0.11 g/g) are added as stabilizers and the mixture is warmed to 37° C. under stirring. The pH is adjusted to 6.8-7.4. The solution is heated to 60°±0.5° C. and maintained at that temperature for 10 hours.

After pasteurization, the stabilizers used for heat treatment are removed by diafiltration and the product is concentrated by ultrafiltration. An affinity chromatography step is then used to remove plasminogen from the product, after which it is concentrated, formulated and sterile filtered. The filtered solution is filled aseptically in 1 ml, 2 ml, or 5 ml aliquots, frozen at ≦−60° C. and stored at −30° C.±5° C. until use.

A second solution containing thrombin may be produced from cryo-poor plasma. The cryo-poor plasma is applied to an anion exchange column for binding to prothrombin and activation into thrombin. The resultant thrombin does not bind to the column and is eluted with calcium chloride. Thrombin may then be subjected to SD treatment for 6 to 6.5 hours at 26° C.±1° C. The SD reagents may be removed by cation exchange chromatography. Mannitol (as a 15% solution), and human albumin may be added to the product as stabilizers to a final concentration of 2% (w/w) and 0.2% (w/w), respectively. The stabilized solution may then be passed through a nanofiltration module.

The filtrate is formulated with calcium chloride to 40 mM and the concentration of human albumin is adjusted to 0.6%. The thrombin bulk solution is sterile filtered and aseptically filled in 1 ml, 2 ml, or 5 ml aliquots, frozen at ≦−60° C., and stored at −30° C.±5° C. until use.

Example 3

Swine Injury Model to Evaluate γA/γ' Fibrinogen Sealant

Degradation-resistant γA/γ' and γA/γA fibrinogen sealants were tested in a randomized prospective, blinded study comparing blood loss after an aortic injury in pigs receiving three different treatments—either standard CROSSEAL™ fibrin sealants (positive control), γA/γ' fibrinogen sealants, or albumin (negative control). The aortic injury model produces reproducible clot failure following aortic injury.

A hole was made in the aorta of pigs with a 2.0 mm skin biopsy punch. The punch was removed and bleeding was initiated. After a 15 minute initial hemorrhage, animals were assigned randomly to a fibrinogen sealant treatment group—CROSSEAL™, degradation-resistant γA/γ' fibrinogen sealants, or albumin control. One of the two types of fibrinogen sealants or albumin was sprayed on the aortic wound using a CROSSEAL™ fibrin applicator (American Red Cross). The investigators were blinded as to the identity of the sealant. A gauze dressing was applied to cover the wound using manual pressure. If hemostasis was incomplete, up to two more applications of sealant and dressing were applied where necessary with two minutes of manual compression as described above. Following application of the sealant, resuscitation was initiated with a 37° C. lactated Ringer's solution at 250 ml/minute with a roller pump. Mean arterial, systolic, and diastolic blood pressures and heart rate are recorded at 10 second intervals throughout the study period using a continuous data collection system. The mean arterial pressure at which re-bleeding occurs, the volume of lactated Ringer's solution required, and the time to re-bleeding were measured. At 60 minutes, surviving animals were killed by an overdose of a commercially available euthanasia solution (Beuthanasia) administered at 1 ml/10 lb i.v. Following completion of the study, intra-abdominal blood loss was measured. Proportions of animals surviving the 60 minute study period were compared. Primary outcome variables were mean arterial bleeding pressure at which re-bleeding occurs, blood loss, mortality, time to death, extent of coagulopathy, resuscitation requirements and acidosis.

As shown in FIG. 1, degradation-resistant γA/γ' fibrinogen sealant of the present disclosure allowed increased arterial pressure without hemorrhage when arterial pressure is restored as compared to albumin or CROSSEAL™ fibrin sealant.

Example 4

Percentage of γA/γ' Fibrinogen Affects Rate of Fibrinolysis

Figure 2:
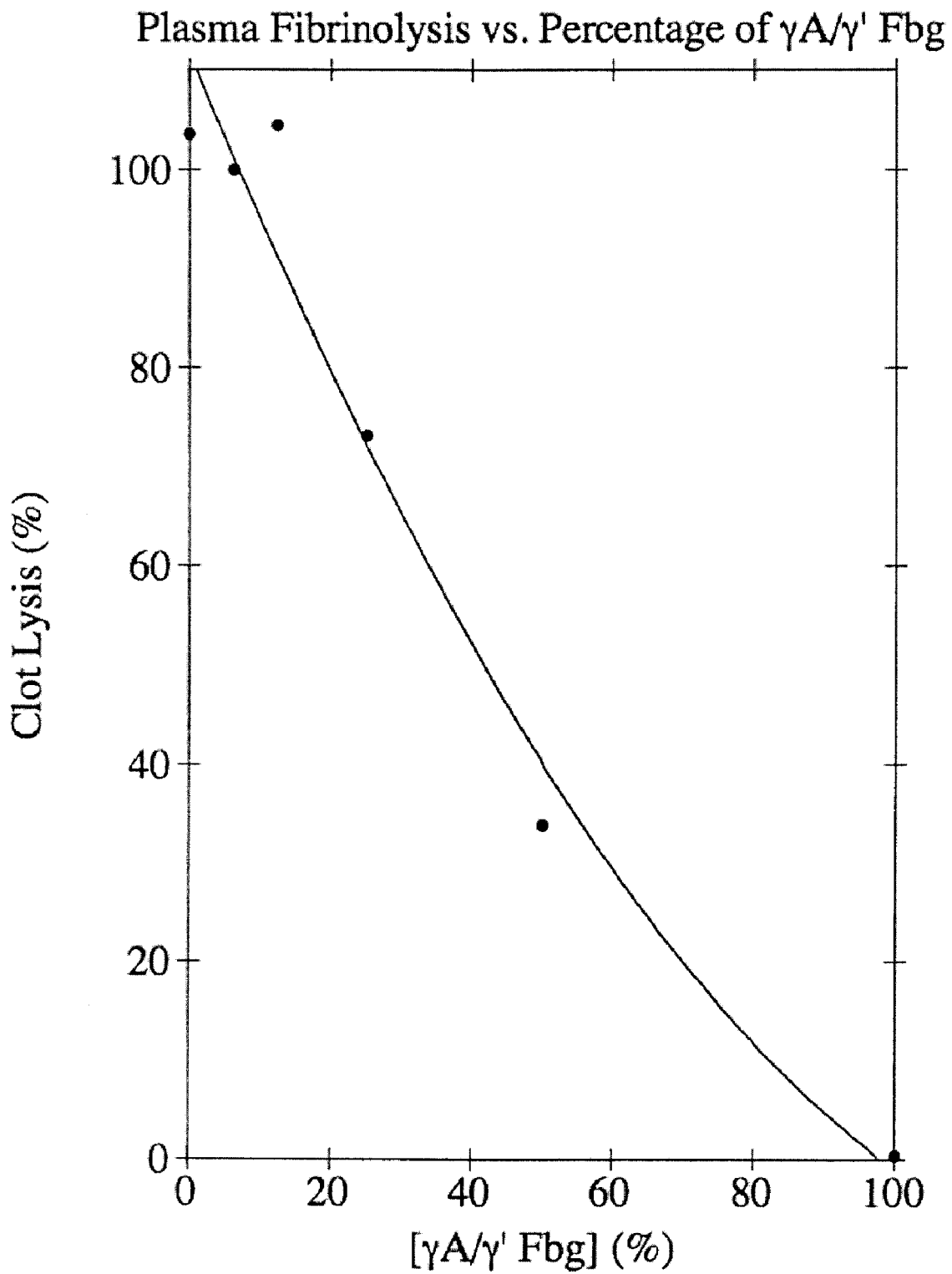
FIG. 2 is a graph representing percentage of clot lysis as a function of the percent of γA/γ' fibrinogen in the clot.

Microtiter plate fibrinolysis assays were carried out as described previously by Jones and Meunier using 96-well assay plates (Corning 25-880-96; Jones and Meunier (1990) *Thromb. Haemostasis* 64:455-463). Fibrinogen and Lys-plasminogen (Calbiochem) were added to an interim mixing plate containing assay buffer (0.1 M NaCl, 30 mM NaHCO$_3$, 4 mM KCl, 1 mM CaCl$_2$, 1 mM Na$_2$HPO$_4$, 0.3 mM MgCl$_2$, 0.4 mM MgSO$_4$, 10 mM HEPES, pH 7.4, 0.01% Polysorbate 80). A separate assay plate contained α-thrombin and tissue plasminogen activator (Calbiochem) in assay buffer. The fibrinogen/plasminogen solution was then dispensed from the interim plate into the assay plate wells containing thrombin and tissue plasminogen activator. The final concentrations of reagents were 1.25 mg/ml fibrinogen, 30 μg/ml Lys-plasminogen, 16 ng/ml tissue plasminogen activator, and 13.2 NIH units/ml thrombin in a total volume of 100 μl. For assays containing Factor XIII, Factor XIII was added to a final concentration of either 10 or 100 μg/ml to the wells in the interim plate containing the plasminogen/fibrinogen mixture. In some assays 1 mM N-ethylmaleimide was also added to the interim plate. The turbidity of the clot was measured at room temperature every 6 minutes at 405 nm. The optical density was converted to percent lysis as follows:

% lysis=($A_{405}$×100%)÷($A_{405}$ maximum)

and plotted versus concentration of γ/γ' fibrinogen (γA/γ' Fbg). See FIG. 2.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A degradation-resistant fibrinogen sealant consisting of a first composition and a second composition;
   wherein said first composition consists of at least one fibrinogen dimer selected from the group consisting of fibrinogen γA/γ' heterodimer and fibrinogen γ'/γ' homodimer and at least one pharmaceutically acceptable carrier, wherein said fibrinogen dimer is present at a concentration of between about 5 mg/ml to about 200 mg/ml; and
   wherein said second composition consists of thrombin and at least one pharmaceutically acceptable carrier, wherein said thrombin is present at a concentration of between about 4 IU/ml and about 1000 IU/ml.

2. The degradation-resistant fibrinogen sealant of claim 1 wherein said fibrinogen dimer is present at a concentration of between about 10 mg/ml to about 200 mg/ml.

3. The degradation-resistant fibrinogen sealant of claim 1 wherein said fibrinogen dimer is present at a concentration of between about 25 mg/ml to about 150 mg/ml.

4. The degradation-resistant fibrinogen sealant of claim 1 wherein said fibrinogen dimer is present at a concentration of between about 40 mg/ml to about 130 mg/ml.

5. The degradation-resistant fibrinogen sealant of claim 1 wherein fibrinogen dimer is present at a concentration of between about 65 mg/ml and about 115 mg/ml.

6. The degradation-resistant fibrinogen sealant of claim 1 wherein said first composition consists of fibrinogen γA/γ' and at least one pharmaceutically acceptable carrier.

7. The degradation-resistant fibrinogen sealant of claim 1 wherein said first composition consists of fibrinogen γ'/γ' and at least one pharmaceutically acceptable carrier.

8. The degradation-resistant fibrinogen sealant of claim 1 wherein said fibrinogen γA/γ' is present at between about 5% and about 90% of total fibrinogen.

9. The degradation-resistant fibrinogen sealant of claim 1 wherein said fibrinogen γA/γ' is present at between about 10% and about 80% of total fibrinogen.

10. The degradation-resistant fibrinogen sealant of claim 1 wherein said fibrinogen γA/γ' is present at between about 20% and about 70% of total fibrinogen.

11. The degradation-resistant fibrinogen sealant of claim 1 wherein said fibrinogen γA/γ' is present at a concentration selected from the group consisting of about 30%, 40%, 50%, and 60% of total fibrinogen.

12. The degradation-resistant fibrinogen sealant of claim 1 wherein said first composition has a pH of between about pH 5.0 and about pH 9.0.

13. The degradation-resistant fibrinogen sealant of claim 1 wherein said first composition has a pH of between about 5.5 and about pH 8.5.

14. The degradation-resistant fibrinogen sealant of claim 1 wherein said first composition has a pH of between about pH 6.0 and about pH 8.0.

15. The degradation-resistant fibrinogen sealant of claim 1 wherein said first composition has a pH of between about pH 6.5 and about pH 7.5.

16. The degradation-resistant fibrinogen sealant of claim 1 wherein said first composition has a pH of between about pH 6.7 and about pH 7.2.

17. The degradation-resistant fibrinogen sealant of claim 1 wherein said thrombin is present at a concentration of between about 15 IU/ml and about 1000 IU/ml.

18. The degradation-resistant fibrinogen sealant of claim 1 wherein said thrombin is present at a concentration of between about 15 IU/ml and about 150 IU/ml.

19. The degradation-resistant fibrinogen sealant of claim 1 wherein said thrombin is present at a concentration of between about 15 IU/ml and about 120 IU/ml.

20. The degradation-resistant fibrinogen sealant of claim 1 wherein said thrombin is present at a concentration selected from the group consisting of about 25 IU/ml, 50 IU/ml, 75 IU/ml, and 100 IU/ml.

21. The degradation-resistant fibrinogen sealant of claim 1 wherein the pH of said second composition is between about pH 5.0 and about pH 9.0.

22. The degradation-resistant fibrinogen sealant of claim 1 wherein the pH of said second composition is between about pH 5.5 and about pH 8.5.

23. The degradation-resistant fibrinogen sealant of claim 1 wherein the pH of said second composition is between about pH 6.0 and about pH 8.0.

24. The degradation-resistant fibrinogen sealant of claim 1 wherein the pH of said second composition is between about pH 6.5 and about pH 7.5.

25. The degradation-resistant fibrinogen sealant of claim 1 wherein the pH of said second composition is between about pH 6.8 and about pH 7.2.

26. The degradation-resistant fibrinogen sealant of claim 1 wherein said fibrinogen dimer is present at a concentration of between about 40 mg/ml to about 130 mg/ml and wherein said thrombin is present at a concentration of between about 15 IU/ml and about 1000 IU/ml.

27. A kit comprising the degradation-resistant fibrinogen sealant of claim 1 and a syringe.

28. A method for the treatment of vascular trauma in a patient, said method comprising the step of administering to said patient the degradation-resistant fibrinogen sealant of claim 1.

* * * * *